United States Patent
Sakadume et al.

(10) Patent No.: US 7,520,912 B2
(45) Date of Patent: Apr. 21, 2009

(54) AIR PURIFYING FILTER MEDIA AND PROCESS FOR PRODUCING THE SAME

(75) Inventors: Nobuyuki Sakadume, Nagaoka (JP); Toshihiko Soyama, Nagaoka (JP); Eiko Meguro, Nagaoka (JP); Kazuro Isomae, Tokyo (JP); Mikiko Gokano, Tokyo (JP)

(73) Assignees: Hokuetsu Paper Mills, Ltd., Nagaoka-shi (JP); Nikki-Universal Co., Ltd., Tokyo (JP)

( * ) Notice: Subject to any disclaimer, the term of this patent is extended or adjusted under 35 U.S.C. 154(b) by 672 days.

(21) Appl. No.: 10/506,520

(22) PCT Filed: Oct. 16, 2002

(86) PCT No.: PCT/JP02/10765

§ 371 (c)(1), (2), (4) Date: Jan. 31, 2005

(87) PCT Pub. No.: WO2004/035173

PCT Pub. Date: Apr. 29, 2004

(65) Prior Publication Data

US 2006/0117958 A1 Jun. 8, 2006

(51) Int. Cl.
*B01D 45/00* (2006.01)
*A61L 9/00* (2006.01)
*C12N 11/14* (2006.01)

(52) U.S. Cl. .............................. 55/524; 55/527; 95/285; 96/226; 422/4; 422/28; 435/176; 435/177; 435/181

(58) Field of Classification Search .................... 55/524, 55/527; 95/285; 96/226; 422/4, 28; 435/176, 435/177, 181
See application file for complete search history.

(56) References Cited

U.S. PATENT DOCUMENTS

| | | | | |
|---|---|---|---|---|
| 5,102,799 A | * | 4/1992 | Urban et al. ................. | 435/180 |
| 5,130,237 A | * | 7/1992 | Thomas et al. ................. | 435/96 |
| 5,395,411 A | * | 3/1995 | Kobayashi .................... | 55/486 |
| 5,527,672 A | * | 6/1996 | Mansfield et al. ............... | 435/6 |
| 5,614,105 A | * | 3/1997 | Heilmann et al. ........... | 210/767 |
| 5,620,706 A | * | 4/1997 | Dumitriu et al. ............ | 424/485 |
| 5,719,228 A | * | 2/1998 | Taylor et al. ................. | 524/593 |
| 5,889,073 A | * | 3/1999 | Zhang et al. .................... | 522/3 |
| 6,228,135 B1 | * | 5/2001 | Sugo et al. ..................... | 55/528 |
| 6,372,472 B1 | * | 4/2002 | Nehls et al. .................. | 435/198 |
| 6,579,352 B1 | * | 6/2003 | Tanaka et al. ................. | 96/226 |
| 6,730,144 B2 | * | 5/2004 | Tanaka et al. ................. | 95/285 |
| 2002/0102180 A1 | * | 8/2002 | Sheldon ......................... | 422/4 |

FOREIGN PATENT DOCUMENTS

| | | |
|---|---|---|
| JP | 2-291264 A | 3/1990 |
| JP | 2-041166 A | 9/1990 |
| JP | 958851 A1 | 11/1999 |
| JP | 2000-334224 | 12/2000 |
| JP | 2007-203295 | 8/2007 |

* cited by examiner

*Primary Examiner*—Duane S Smith
*Assistant Examiner*—Minh-Chau T Pham

(57) ABSTRACT

It is intended to provide an air purification filter which has a high dry tensile strength, a high wet tensile strength in association with a high water resistance and a high water repellency and exhibits a bactericidal effect due to a gas phase reaction in a gas phase. Namely, an air purification filter having a high dry tensile strength, a high wet tensile strength (a high water resistance) and a high water repellency as well as a bactericidal effect which is obtained by blending a filter fiber having a functional group with a mixture of a modification enzyme which has an ionic polarity opposite to the ionic polarity of the whole filter fiber as described above and a bactericidal effect with an ionic synthetic resin binder having the opposite ionic polarity similar to the modification enzyme.

59 Claims, No Drawings

AIR PURIFYING FILTER MEDIA AND PROCESS FOR PRODUCING THE SAME

TECHNICAL FIELD

This invention relates to an air purifying filter media having a high water resistance and a high repellency as well as exhibiting bactericidal/sterilizing or antimicrobial means properties using enzyme reaction in a gas phase.

RELATED ART

Air purifying filter media of the related art capture primarily suspended particles such as dust and fine particles on which microorganisms such as bacteria are deposited, in air. In the conventional air purifying filter media, the microorganisms captured on the filter media may grow and scatter based on the nutritional source existing in the dust. Today, this situation is regarded as a problematic matter. Namely, it may cause secondary contamination. Therefore, recently, a development of an air filter media that exhibits bactericidal/sterilizing or antimicrobial means properties using enzyme has been attempted. Among the prior art, filter media in which a silver complex ion as an antibacterial agent was fixed by a binder, has been provided (see, for example, Patent Literature 1). However, in this technique, as the binder deteriorates, silver itself falls off from the filter media in the form of a powder, and, after the silver complex ion performs an antimicrobial reaction, it will not achieve the expected result because the antimicrobial reaction cannot occur again. Therefore, new treatment of the surface is required, so that this process requires time and expense and, furthermore, an original function of the filter media is inhibited. Furthermore, another disadvantage of this process is that silver itself has a high price.

An antimicrobial air filter prepared by impregnating it with a binder liquid containing a thiabendazole-based chemical and an inorganic powder containing silver as an antimicrobial agent to a wet paper web consisting of the air filter glass fiber is proposed (see, for example, Patent Literature 2). However, in this case, there is such a problem that, as time passes, the antimicrobial effect is lost due to high volatility of the thiabendazole-based chemical. Also, this process has a problematic matter that the silver-containing inorganic powder causes a falling in the form of a powder due to a deterioration of the binder applied to the filter media. Recently, a technique in which an enzyme is used as a sterilizing, bactericidal and antimicrobial mean is provided. Among related art techniques, it is provided that, as a carrier on which lytic enzyme having sterilizing properties is immobilized, a nonwoven fabric containing a natural fiber or chemical fiber, or a mixture thereof as a web-consisting fiber is employed (see, for example, Patent Literature 3). Furthermore, as a carrier on which an enzyme is immobilized, ceramic, glass or organic high molecular materials in the form of porous film, fiber, spun fiber as well as woven network prepared by knitting fiber or spun fiber, or particle is provided (see, for example, Patent Literature 4).

However, both these related arts are based on a liquid phase reaction in which sterilizing properties are developed only in the presence of water, and are not based on a gas phase reaction attended with sterilizing properties.

Furthermore, a filter media containing a glass fiber as main fiber, on which the enzyme is immobilized and which a repellent treatment is not performed, has a high antimicrobial effect. For example, immobilizing enzyme on silica glass fiber is possibly due to having hydroxyl group on its surface (see, for example, Patent Literature 5).

In the filter media on which the enzyme is immobilized, the filter media tend to lower water resistance and the repellency effect because the enzyme is immobilized to a fiber without a repellency treatment. Recently, in a lot of fields such as in the filter media for a fan coil, which is used frequently in a high humidity atmosphere, or in prevention of soaking up a sealing agent during processing a filter media, etc., a high water resistance (a high wet tensile strength), and an improved repellency which can repel humidity and drops of water is demanded. Examples of the demand as a strength against wetness in the case of its use in humidity during a ventilation or in outdoors are a dry tensile strength of 0.45 kN/m or more in a machine direction and 0.35 kN/m or more in a cross direction and a wet tensile strength of 0.176 kN/m in a cross direction of the filter media, according to a method of measurement defined in MIL-F-51079 C respectively. Furthermore, the repellency of 508 mm or more (the height of the water column), defined in MIL-282, is desired simultaneously. It can be regarded that, in order to achieve it, a repellent is applied to the enzyme-immobilized filter media of the said Patent Literature 5. However, in this filter media, a repellent-untreated surface of the fiber is a precondition for the absolute immobilization of the enzyme on the surface of the fiber. Since the repellent treatment after the enzyme immobilization, in order to achieve the high repellency, lowers the activity of the enzyme, it was difficult to simultaneously achieve a high water resistance and a high water repellency.

Furthermore, as a related art, a process for the preparation of a usual air filter media is provided (see, for example, Patent Literature 6). The herein provided process for the preparation of a usual air filter media comprised applying a solution containing an organic synthetic resin binder, polyisocyanate compound and repellent to glass fiber constituting an air filter media and drying so that a satisfactory strength of the filter media, such as a high dry tensile strength and a high wet tensile strength, is achieved.

However, after dehydrating an air filter media fiber and forming, the solution containing the organic synthetic resin binder, polyisocyanate compound and repellent is mixed with the enzyme and the resulting mixture is applied only to a filter media fiber according to this preparation process, sufficient strength of the filter media, such as a dry tensile strength and a wet tensile strength is not achieved. If this related art is copied simply, the enzyme is taken into synthetic resin binder film, a part in which the enzyme was taken into is heterogeneous concerning a fixing between each filter media fiber so that a development of binding strength between each fiber is hindered. As a result, a deterioration of the dry tensile strength and the wet tensile strength occurs. Furthermore, since the synthetic resin binder hinders a binding between fiber and the enzymes by covering the enzyme with a film of the synthetic resin binder, the enzyme is in a heterogeneously fixing state on the filter media fiber so that its sterilizing properties are lost.

Patent Literature 1: JP-A-2000-288323, page 3, left column,

Patent Literature 2: JP-A-8-144199, page 2, left column to page 3, right column, Patent Literature 3: JP-A-60-49795, page from 1 to 2, Patent Literature 4: JP-A-2-4116, page from 1 to 2, FIGS. 1 to 3, Patent Literature 5: WO 98/04334, page 3, lower left column to page 4, upper right column, Patent Literature 6: JP-A-9-225226, page 2, right column to page 3, right column.

OBJECT TO BE SOLVED BY THE INVENTION

It is therefore an object of the invention to provide an air purifying filter media immobilized by the enzyme, which improves the bactericidal/sterilizing or antimicrobial means properties using enzyme, and also improves a high dry tensile strength and a high wet tensile strength in association with a high water resistance, and a high repellency.

MEANS FOR SOLVING THE OBJECT

This object was solved by an air purifying filter media having bactericidal/sterilizing or antimicrobial means properties using enzyme reaction, which is obtained by applying a mixture of the modified enzyme which has an ionic polarity opposite to the ionic polarity of the whole filter media fiber having a functional group, and which has sterilizing properties, with an ionic synthetic resin binder having the opposite ionic polarity similar to the modified enzyme, to the whole filter media fiber, as described above. This filter media also has an outstanding water resistance and an excellent repellency.

The filter media fiber of the air purifying filter according to the invention is not limited in any particular way as long as it is capable of performing as an air purifying filter media and has a functional group. Preferably, it is at least one of a group consisting of boron-silica glass fibers, alkyl amine glass fibers, silica-alumina fibers, rayon fibers, cotton fibers, hemp fibers, wool fibers, polyamide fibers, polyvinyl alcohol fibers, acetate fibers, polyacrylamide fibers or a copolymer thereof.

The functional group which the air purifying filter media fibers, used according to the invention, possess, is at least one of a group consisting of hydroxyl and carboxyl group having an anionic polarity, and an amino and an imino group having a cationic polarity.

When the modified enzyme is used in a mixture with an ionic synthetic resin binder, in case they have the same polarity as each other, the mixture is in a stabile state without an occurrence of an interferential action. In case they have different polarities, the interferential action occurs with both materials so that a new compound is produced. As a result, they cannot coexist as a stabile mixture. Therefore both materials used must possess the same ionic polarity.

Most of the modified enzyme immobilized to the functional group of the filter media fiber has plural groups selected from a group consisting of an amino and carboxyl group and others. The polar condition is largely variable depending on the external environment such as pH (hydrogen ion concentration). Concerning the optimum pH-width of the modified enzyme, there is a wide case or a narrow case, where each of the modified enzymes has a different optimum pH-width. The modified enzymes having the ionic polarity opposite to the ionic polarity of the filter media fiber become easily chemically binding, for example in a form of covalent bond or ionic bond to the filter media fiber optionally by controlling pH-value, so that the strength binding with the fiber is achieved.

Such the modified enzyme is preferably at least one enzyme modified with at least one compound selected from a group consisting of N-substituted carbamate bromide, N-substituted imide carbonate bromide, acetyl bromide+triacetyl cellulose, dimethylaminoethyl, diethylaminoethyl, protamine, polyethylene imine, polyvinyl amine, polyallyl amine, polylysine, polyornitine, dextran, dextran sulfate, dextrin and chondroitin sulfate.

The modified enzyme used according to the invention is not limited in any particular way, but preferably is at least one selected from a group consisting of β-1,3-glucanase, chitinase, lysozyme, protease, glucosidase, β-galactosidase, endo-β-N-acetylglucosamidase and endolysin.

Binder is used mainly in order to bind fibers to each other and to finish the form of the filter media, and for this reason is necessary for the preparation of the filter media.

The ionic synthetic resin binders having an ionic polarity opposite to the ionic polarity of the filter media fiber are a cationic synthetic resin binder or an anionic synthetic resin binder. The cationic synthetic resin binder has a weak to strong cationic property, while the anionic synthetic resin binder has a weak to strong anionic property.

The cationic synthetic resin binder is acrylic resin, for example, Light-Epoch®BX-71 (maker: KYOUEISYA CHEMICAL Co., Ltd.), urethane resin, for example, Super-Flex® 600 (maker: DAI-ICHI KOGYO SEIYAKU CO., LTD.), vinyl acetate resin, for example, Movinyl® 350 (maker: Clariant polymer Cop., Ltd.), SBR resin, for example, Cementex® C220T (maker: Obanaya Cementex Co. Ltd.), Epoxy resin, for example, Santax® P-5500 (maker: Mitsui Chemicals Inc.), polyvinyl alcohol resin, for example, C-506 (maker: Kuraray Co., Ltd.). Among these cationic synthetic resins, at least one is used.

The anionic synthetic resin binder is at least one selected from a group consisting of acrylic resin, Voncoat® AN-155 (maker: DAINIPPON INK AND CHEMICALS INC.), urethane resin, Super-flex® 700 (maker: DAI-ICHI KOGYO SEIYAKU CO., LTD.), vinyl acetate resin, for example, Movinyl® 303 (maker: Clariant polymer Cop. Ltd.), SBR resin, for example, Lacstar® 7300A(maker: DAINIPPON INK AND CHEMICALS INC.), Epoxy resin, for example, Dicfine® EN-0270 (maker: DAI NIPPON INK AND CHEMICALS INC.), polyvinyl alcohol resin, for example, KL-318 (maker: Kuraray Co., Ltd.). Among these anionic synthetic resins, at least one is used.

It is shown that the effect concerning a high dry tensile strength, a high wet tensile strength developing a high water resistance, and a high repellency, which cannot be achieved by each of the said ionic synthetic resin binders and the modified enzymes, is developed by the combination of both.

If the functional group of the filter media fibers to be used has an anionic polarity such as hydroxyl and carboxylic group, using the cationic synthetic resin binder is most suitable. While, if the functional group of the filter media fibers to be used has a cationic polarity such as an amino group, using the anionic synthetic resin binder is most suitable. This combination is an embodiment of the inventive process for the preparation of the filter media on which the modified enzyme is immobilized.

When the ionic synthetic resin is selected, in case the functional group of the filter media fiber used is an anion group such as hydroxyl and carboxylic group, selecting a cationic synthetic resin is most suitable.

If the functional group of the filter media fiber has a cationic polarity, as an amino group, selecting an anionic synthetic resin binder is most suitable.

If the mixture consisting of the said fiber having an anionic polarity and the fiber having a cationic polarity is used, the modified enzyme and the ionic synthetic resin binder must be so selected that they are suited to the fiber accounting for a major mixing proportion.

If using the said ionic synthetic resin binder and the modified enzyme is unsatisfactory for a desired repellency, a water repellent agent can be also used in order to supplement a repellency of the filter media. A fluorine compound repellent is very suitable to annex high water repellency and high oil repellency to the filter media, because it gives not only water repellency but also oil repellency to the filter media.

However, in case a large amount of the repellent is applied to the filter media, the sterilizing properties of the modified enzyme are decreased. Therefore, in order to keep a sterilization ratio of 99.9% or more, it is desired that the applied amount of the repellent is limited to a minimum amount.

The applied amount of the repellent is below 0.1% by weight, preferably below 0.08% by weight based on the weight of the filter media.

In addition to the ionic synthetic resin binder used in the invention, an internal fibrous binder such as polyvinyl alcohol fiber, olefin fiber, etc., can be used without a problem, because they do not prevent the effect achieved by the invention.

Viewed in the practical economy, an embodiment of the process for the preparation of the enzyme-immobilized filter media of the invention is shown as follows:

The filter media fibers used are selected in a most suitable mean fiber-diameter thereof in consideration for desired physical properties such as a pressure drop, a filter media collection efficiency and basis weight of the filter media and are compounded with each other. In the case of one example of the high efficiency particulate air filter media (HEPA filter media), a compound consisting of 95% of an ultrafine glass fiber of 3 μm or less, a mean diameter, and 5% of a chopped strand glass fiber is used. In the case of one example of the middle efficiency air filter media, a compound consisting of 50% of an ultrafine glass fiber of 3 μm or less in mean diameter and 50% of a chopped strand glass fiber is used.

The ionic synthetic resin binder having the same polarity as that of the modified enzyme has compatibility with the latter so that it possess an advantageous property that it is not easily interfered with. After preparation of a slurry containing both fibers having a different diameter by using this property for obtaining the desired filter media, to a wet paper web produced from the slurry under dehydration by using a wet-type paper machine or a dried paper thereof is applied a mixture (in a solution or dispersion) consisting of the modified enzyme and an ionic synthetic resin binder and, if desired, a repellent. This enables the uniform immobilization of the modified enzyme to the filter media fiber and uniform adherence of the ionic synthetic resin binder to the filter media fiber.

Herein, a wet paper web is that which has a water content of from 10% to 90%, preferably from 20% to 80%, while a dry paper is that which has water content of 10% or less. An application of a mixture consisting of the modified enzyme and an ionic synthetic resin binder on a wet paper web or a dry paper is preferably carried out before following the paper-making step, for example dehydration and/or washing and/or drying step, but it can be effected by applying the mixture of the modified enzyme and an ionic synthetic resin binder on the dry paper, by washing and again drying.

A method for applying the modified enzyme and an ionic synthetic resin binder is a dipping method, a spraying method, roll transcribing method, etc. Cylinder dryer, Yankee dryer, through dryer, rotary dryer or infrared dryer, etc., can be used for the drying method. Furthermore, 2 types of dryer may be also used for drying the inventive filter media, without prevention.

An embodiment of the process of the invention is shown as follows:

The slurry compounded a fiber having a diameter suitable for the desired filter media is prepared, thereafter the said slurry is dehydrated in a paper-making machine to form a wet paper web, and this wet paper web is impregnated in an aqueous solution containing the modified enzyme and an ionic synthetic resin binder, dehydrated and, if desired, washed with water and dried by the rotary dryer.

In this drying step, in order to develop simultaneously high sterilizing properties, a high dry tensile strength and a high wet tensile strength, as well as a high water repellency, the preferable reaction time and the reaction temperature range, as well as the optimal amount of the modified enzyme and the ionic synthetic resin binder, have importance for optimally immobilizing the enzyme by the chemical binding between the functional group of the filter media fiber and the modified enzyme, such as a covalent bond or ionic bond, etc.

As a result of our verification, when the temperature of the drying step is less than 80° C., the immobilization of the modified enzyme by the chemical bond between the filter media fiber and the modified enzyme is not progressed virtually, and the wet tensile strength and the repellency are not developed, because there is no development of the strength based on the solidification of the ionic synthetic resin binder. In case the drying temperature is more than 220° C., the high dry tensile strength and the high wet tensile strength are achieved, but the sterilizing properties of the modified enzyme decrease. Therefore, the temperature of the drying step is between 80° C. to 220° C., and preferably 100° C. to 200° C.

If the amount of the ionic synthetic resin binder is less than 0.1% by weight, based on the filter media after drying, an effect required for a practical use is not achieved. If that amount is more than 10.0% by weight, the pressure drop of the filter media increase, physical properties such as dust particles collection efficiency as a filter media decrease, and at the same time, the sterilizing properties also decrease by coating a part of the modified enzyme with an ionic synthetic resin binder. Therefore, the suitable amount of the ionic synthetic resin binder is 0.1 to 10.0% by weight, and preferably 0.5 to 7.0% by weight.

If the amount of the modified enzyme is also less than 0.01% by weight, based on the dried filter media, an effect required for a practical use is not achieved. The upper limit thereof is equivalent to the number of the functional group. For example, in case the fiber is boron silica fiber having many functional groups, it is 4.0% by weight. If more than this is used, only the number of the functional groups is immobilized on the filter media fiber. Therefore, the suitable amount is 0.01% by weight or more, and preferably 0.05% by weight or more.

The invention enables the satisfactory, simultaneous effect of the high dry tensile strength and the high wet tensile strength, as well as the high water repellency of the filter media without decreasing the sterilizing properties and the dust collection efficiency. As a result, the use of the filter media in an environment of high humidity in which using a filter media was difficult until today is enabled. By using the inventive air purifying filter media having the sterilizing properties the microorganism floated in air, such as bacteria and fungi is collected by the filter media, even if in an environment which an absolute humidity of the air is 100 ppm or more, glycoside, amide, peptide, etc., which construct a cell wall, are cut by hydrolysis, the microorganism is ruptured at the cut part of its cell wall by osmotic pressure and dies out. As a result, this mechanism leads to a bactericidal, bacteria-removal, bacteriostatic effect, and then a growth and scatter of the microorganism is prevented and a secondary pollution is kept out.

The air filter media by which the secondary pollution is kept out like this can be used in an industrial or domestic field that requires an air filter media. Preferably, it is most suitable for business in a food factory, a drink factory, a pharmaceutical factory, facilities for experiment on animals, facilities for a hospital, facilities for a semiconductor, facilities for bio-science, etc.

The present invention will be described below in detail with reference to Examination, Comparative Examples and Tests. It should, however, be noted that the invention is in no way limited by those Examples.

EXAMPLES

Example 1

95% ultrafine glass fiber of 3 μm or less in mean diameter, which has hydroxyl group as a functional group having an anionic polarity, and the 5% chopped strand glass fiber of 9 μm in mean diameter were dispersed in 0.4% aq. solution in 1 m$^3$ acid water (pH 3.5) in a pulper to prepare a slurry. A wet paper web was produced from this slurry under dehydration by using a wet-type paper machine. The wet paper web was impregnated with a mild acidic aq. solution of pH 4.5 so as to apply the modified enzyme contained 3% by weight β-1,3-glucanase modified with bromide N-substituted carbamate and 3% by weight cationic synthetic resin binder (Light-Epoch® BX-71, KYOUEISYA CHEMICAL Co., Ltd.) based on the weight of the dried filter media, respectively. After dehydration it was dried by rotary drier at 120° C. to obtain HEPA filter media 1A having a basis weight of 63 g/m$^2$.

Example 2

95% ultrafine glass fiber of 3 μm or less in mean diameter, which has hydroxyl group as a functional group having an anionic polarity, and the 5% chopped strand glass fiber of 9 μm in mean diameter were dispersed in 0.4% aq. solution in 1 m$^3$ acid water (pH 3.5) in a pulper to prepare a slurry. A wet paper web was produced from this slurry under dehydration by using a wet-type paper machine. The wet paper web was dried by rotary drier to obtain a dry paper. The dry paper was impregnated with a mild acidic aq. solution of pH 4.5, so as to apply the modified enzyme contained 3% by weight β-1,3-glucanase modified with bromide N-substituted carbamate and 3% by weight cationic synthetic resin binder (Light-Epoch® BX-71, KYOUEISYA CHEMICAL Co., Ltd.) based on the weight of the dried filter media, respectively. Thereafter it was dehydrated, washed and dried by rotary drier at 120° C. to obtain filter media 2A having a basis weight of 63 g/m$^2$.

Example 3

The procedure of Example 1 was repeated, except that the 50% ultrafine glass fiber of 3 μm or less in mean diameter, which has hydroxyl group as a functional group having an anionic polarity, and the 50% chopped strand glass fiber of 9 μm in mean diameter, were dispersed in 0.4% aq. solution in 1 m$^3$ acid water (pH 3.5) by a pulper to prepare a slurry to obtain ASHRAE filter media 3A having a basis weight of 63 g/m$^2$.

Example 4

The procedure of Example 1 was repeated, except that, in Example 1, 0.03% by weight of fluorine compound repellent (Light-guard® FRG-1, KYOUEISYA CHEMICAL Co., Ltd.) based on weight of the filter media was applied to the wet paper web simultaneous with the modified enzyme and the cationic synthetic resin binder. HEPA filter media 4A having a basis weight of 63 g/m$^2$ was produced.

Example 5

The procedure of Example 1 was repeated, except that 100% by weight of Rayons fiber of 17 μm in mean diameter (3.3 Detx×5 mm, Cut goods, Daiwabo Rayon Co., Ltd.), which has hydroxyl group as a functional group having an anionic polarity was dispersed in 0.4% aq. solution in Jm$^3$ acid water (pH 3.5) by a pulper to prepare a slurry. ASHRAE filter media 5A having a basis weight of 63 g/m$^2$ was obtained.

Example 6

95% ultrafine glass fiber of 3 μm or less in mean diameter and having hydroxyl group as a functional group having an anionic polarity, and the 5% chopped strand glass fiber of 9 μm in mean diameter were dispersed in 0.4% aq. solution in 1 m$^3$ acid water (pH 3.5) by a pulper to prepare a slurry. A wet paper web was produced from this slurry under dehydration by using a wet-type paper machine. The wet paper web was impregnated with a mild acidic aq. solution of pH 4.5 so as to apply the modified enzyme containing 1.5% by weight protease modified with polyallylamine and 1.5% by weight β-1,3-glucanase modified with polyallylamine as well as 3% by weight cationic synthetic resin binder (Light-Epoch® BX-71, KYOUEISYA CHEMICAL Co., Ltd.) based on the weight of the dried filter media, respectively. Thereafter it was dehydrated, dried by rotary drier at 120° C. to obtain HEPA filter media 6A having a basis weight of 63 g/m$^2$.

Example 7

95% ultrafine glass fiber of 3 μm or less in mean diameter and having hydroxyl group as a functional group having an anionic polarity, and 5% chopped strand glass fiber of 9 μm in mean diameter were dispersed in 0.4% aq. solution in 1 m$^3$ acid water (pH 3.5) by a pulper to prepare a slurry. The wet paper web was produced from this slurry under dehydration by using a wet-type paper machine. The wet paper web was impregnated with a mild acidic aq. solution of pH 4.5 so as to apply the modified enzyme containing 1% by weight protease modified with polyornitine, 1% by weight β-1,3-glucanase modified with polyornitine and 1% by weight lysozyme modified with polyornitine as well as 3% by weight cationic synthetic resin binder (Light-Epoch® BX-71, KYOUEISYA CHEMICAL Co., Ltd.) based on the weight of the dried filter media, respectively. Thereafter it was dehydrated, dried by rotary drier at 120° C. to obtain HEPA filter media 7A having a basis weight of 63 g/m$^2$.

Example 8

100% ion-exchange resin fiber of 30 μm in mean diameter, which has an amino group as a functional group having a cationic polarity (IEF-WA, Nitivy Co., Ltd.) was dispersed in 0.4% aq. solution in 1 m$^3$ mild alkali water (pH 8.5) by a pulper to prepare a slurry. A wet paper web was produced from this slurry under dehydration by using a wet-type paper machine. The wet paper web was impregnated with a mild alkaline aq. solution of pH 8.5 so as to apply the modified enzyme containing 3% by weight β-1,3-glucanase modified with polyornitine and 3% by weight anionic synthetic resin binder (Voncoat® AN-155, DAINIPPON INK AND CHEMICALS INC.) based on the weight of the dried filter media, respectively. By this pH-control the modified enzyme indicated an anionic polarity. Thereafter it was dehydrated, dried by rotary drier at 120° C. to obtain ASHRAE filter media 8A having a basis weight of 63 g/m$^2$.

Example 9

The procedure of Example 1 was repeated, except that, in Example 1, the amount of the modified enzyme was replaced by 0.02% by weight. HEPA filter media 9A having a basis weight of 63 g/m² was produced.

Example 10

The procedure of Example 1 was repeated, except that, in Example 1, the amount of the cationic synthetic resin binder was replaced by 6% by weight based on the weight of the dried filter media. HEPA filter media 10A having a basis weight of 63 g/m² was produced.

Example 11

The procedure of Example 1 was repeated, except that, in Example 1, 70% ultrafine glass fiber of 3 μm or less in mean diameter, which has hydroxyl group as a functional group having an anionic polarity, and 30% ion exchange resin fiber of 30 μm in mean diameter were mixed in a pulper. HEPA filter media 11A having a basis weight of 63 g/m² was produced.

Comparative Example 1

The procedure of Example 1 was repeated, except that, in Example 1, the to be applied, modified enzyme mixture was omitted. HEPA filter media 1X having a basis weight of 63 g/m² was produced.

Comparative Example 2

The procedure of Example 1 was repeated, except that, in Example 1, the to be applied cationic synthetic resin binder was omitted. HEPA filter media 2X having a basis weight of 63 g/m² was produced.

Comparative Example 3

The procedure of Example 1 was repeated, except that, in Example 1, the to be applied cationic synthetic resin binder was replaced by the nonionic synthetic resin binder (MD-61, NIPPON NSC LTD.). HEPA filter media 3X having a basis weight of 63 g/m² was produced.

Comparative Example 4

The procedure of Comparative Example 4 was repeated, except that, in Comparative Example 4, in the step in which 3% by weight of the modified enzyme, 3% by weight of the cationic synthetic resin binder and 3% by weight of the water- and oil-repellent agent (Light-guard FRG-1, KOUEISYA CHEMICAL Co., Ltd.) were added additionally. HEPA filter media 4Y having a basis weight of 63 g/m² was produced.

Comparative Example 5

The procedure of, Comparative Example 4 was repeated, except that, in Comparative Example 4, the to be applied cationic synthetic resin binder was replaced by the nonionic synthetic resin binder (MD-61, NIPPON NSC LTD.). HEPA filter media 5Y having a basis weight of 63 g/m² was produced.

Comparative Example 6

The procedure of Example 5 was repeated, except that, in Example 5, the to be applied modified enzyme was omitted. ASHRAE filter media 6X having a basis weight of 63 g/m² was produced.

Comparative Example 7

The procedure of Example 5 was repeated, except that, in Example 5, the to be applied cationic synthetic resin binder was omitted. ASHRAE filter media 7X having a basis weight of 63 g/m² was produced.

Comparative Example 8

The procedure of Example 5 was repeated, except that, in Example 5, the to be applied cationic synthetic resin binder was replaced by the nonionic synthetic resin binder (MD-61, NIPPON NSC LTD.). ASHRAE filter media 8X having a basis weight of 63 g/m² was produced.

Comparative Example 9

The procedure of Example 6 was repeated, except that, in Example 6, the to be applied cationic synthetic resin binder was replaced by the nonionic synthetic resin binder (MD-61, NIPPON NSC LTD.). HEPA filter media 9X having a basis weight of 63 g/m² was produced.

Comparative Example 10

The procedure of Example 6 was repeated, except that, in Example 6, the to be applied cationic synthetic resin binder was replaced by the anionic synthetic resin binder (Voncoat® AN-155, DAINIPPON INK AND CHEMICALS INC.). HEPA filter media 10X having a basis weight of 63 g/m² was produced.

Comparative Example 11

The procedure of Example 7 was repeated, except that, in Example 7, the rotary drier temperature of 120° C. was replaced by 50° C. HEPA filter media 11X having a basis weight of 63 g/m² was produced.

Comparative Example 12

The procedure of Example 7 was repeated, except that, in Example 7, the rotary drier temperature of 120° C. was replaced by 230° C. HEPA filter media 12X having a basis weight of 63 g/m² was produced.

Comparative Example 13

The procedure of Example 8 was repeated, except that, in Example 8, the to be applied cationic synthetic resin binder was replaced by the nonionic synthetic resin binder (MD-61, NIPPON NSC LTD.). ASHRAE filter media 13X having a basis weight of 63 g/m² was produced.

Test 1: Water repellency
This test was carried out in accordance with MIL-282.

Test 2: Dry tensile strength and wet tensile strength
This test was carried out in accordance with MIL-F-51079.

Test 3: Pressure drop

When the face velocity of 5.3 cm/sec passed to the filter media having an effective area of 100 cm², a difference of the pressure was measured by manometer.

Test 4: 0.3 μm DOP collecting efficiency

The DOP collecting efficiency was measured by the laser particle counter, when the air contained DOP particles which was generated by the Laskin nozzle was passed to the filter media having an effective area of 100 cm², in the face velocity of 5.3 cm/sec, wherein the diameter of the objective particle is 0.3 μm.

heart infusion media, centrifuged and washed, was atomized on all required filter media papers in order to evaluate it.

(2) After the said filter media papers were dried in air in a bio-safety-cabinet for a prescribed period, a bacterium was extracted by using a phosphate buffer solution in the violating mixer (or Stomacher®).

(3) The extracted undiluted solution and the diluted solution were transplanted into the natural agar medium.

(4) After 48-hours of cultivation, the colony count was measured, and the living bacteria were calculated.

Result 1:

|  | 1A | 2A | 3A | 1X | 2X | 3X |
|---|---|---|---|---|---|---|
| Fiber material | Glass fiber having OH group | Glass fiber having OH group | Glass fiber having OH group | Glass fiber having OH group | Glass fiber having OH group | Glass fiber having OH group |
| Impregnated Condition | Wet paper web | Dry paper | Wet paper web | Wet paper web | Wet paper web | Wet paper web |
|  | HEPA filter media | HEPA filter media | ASHRAE filter media | HEPA filter media | HEPA filter media | HEPA filter media |
| Binder | Cationic | Cationic | Cationic | Cationic | None used | Anionic |
| Enzyme | Modified enzyme | Modified enzyme | Modified enzyme | None used | Modified enzyme | Modified enzyme |
| Pressure drop (Pa) | 285 | 288 | 38 | 285 | 282 | 280 |
| 0.3 μm DOP collecting efficiency (%) | 99.9914 | 99.9927 | 73.00 | 99.9914 | 99.9912 | 99.9911 |
| PF-Value | 14.0 | 14.1 | 14.2 | 14.0 | 14.1 | 14.2 |
| Water repellency (mm: height of water column) | 550 | 560 | 520 | 50 | 220 | 80 |
| Dry tensile strength (kN/m) | 1.27 | 1.26 | 1.45 | 0.64 | 0.01 or less | 0.25 |
| Wet tensile strength (kN/m) | 0.42 | 0.43 | 0.41 | 0.10 | 0.01 or less | 0.10 |
| Sterilization ratio |  |  |  |  |  |  |
| Test A | 99.99 or more | 99.99 or more | 99.99 or more | Without effect | 99.99 or more | 99 |
| Test B | 99.99 or more | 99.99 or more | 99.99 or more | Without effect | 99.99 or more | 99 |
| Test C | 99.99 or more | 99.99 or more | 99.99 or more | Without effect | 99.99 or more | 99 |

Test 5: PF-Value

This value is a guidepost of filter media efficiency and was determined based on the pressure drop and the DOP collecting efficiency according to the following formula I. A larger value is judged to be a better filter media efficiency.

PF-Value=[LOG 10 {(100−DOP collecting efficiency)/100}×(−100)]/(pressure drop/9.81)   Formula 1

Test 6: Bactericidal/sterilizing evaluation

The test piece having an area 25 cm² (dimension: 5×5 cm) was prepared by cutting a cut sample.
In Test A; *Micrococcus luteus* cells were atomized to the test piece.
In Test B; *Bacillus subtilis* cells were atomized to the test piece.
In Test C; *Staphlococcus aureus* cells were atomized to the test piece.

A sterilization ratio of the atomized bacteria is calculated as a percentage.

Summary of These Tests Will be Explained as Follows:
(1) A aqueous solution (concentration: 1×10⁷ CFU/filter media) of the to be tested bacteria which was cultured in the When the filter media of Examples 1, 2 or 3 in which the modified enzyme having cationic polarity and the cationic synthetic resin binder were opposite polarity of the glass fiber having hydroxyl group as the functional group having the anionic polarity, the sterilizing properties, the sterilization ratio, of 99.99% or more, and the wet tensile strength of 0.42, 0.43 and 0.41 kN/m were achieved. However, in case of Comparative Example 1X in which the modified enzyme was not used, there is no sterilizing properties, and also the water repellency and the wet tensile strength were extremely worse. In the case of Comparative Example 2X in which the ionic synthetic resin binder was not used, but in which the modified enzyme was used, the wet tensile strength was 0.01 or less. In the case of Comparative Example 3X in which the nonionic synthetic resin binder was used, the water repellency is worse, and the sterilization ratio was 99%, that is, insufficient. As above-mentioned result, the filter media of Example 1A shows that, in case of using the mixture of the modified enzyme having cationic polarity and the cationic synthetic resin binder were opposite polarity of the glass fiber having hydroxyl group as the functional group having the anionic polarity is used, all of the water repellency, the dry tensile strength and the wet tensile strength are achieved effectively.

Result 2:

|  | 1A | 4A | 4Y | 3X | 5Y |
|---|---|---|---|---|---|
| Fiber material | Glass fiber having OH group | Glass fiber having OH group | Glass fiber having OH group | Glass fiber having OH group | Glass fiber having OH group |
| Impregnated Condition | Wet paper web HEPA filter media | Wet paper web HEPA filter media | Wet paper web HEPA filter media | Wet paper web HEPA filter media | Wet paper web HEPA filter media |
| Binder | Cationic | Cationic | Cationic | Nonionic | Nonionic |
| Enzyme | Modified enzyme | Modified enzyme | Modified enzyme | Modified enzyme | Modified enzyme |
| Repellent | No | 0.03% by weight | 3.0% by weight | None used | 3.0% by weight |
| Pressure drop (Pa) | 285 | 291 | 286 | 280 | 281 |
| 0.3 μm DOP collecting efficiency (%) | 99.9914 | 99.9945 | 99.9900 | 99.9911 | 99.9890 |
| PF-Value | 14.0 | 14.5 | 13.7 | 14.2 | 13.8 |
| Water repellency (mm: height of water column) | 550 | 1020 | 1020 | 80 | 550 |
| Dry tensile strength (kN/m) | 1.27 | 1.35 | 1.27 | 0.25 | 0.25 |
| Wet tensile strength (kN/m) | 0.42 | 0.45 | 0.42 | 0.10 | 0.10 |
| Sterilization ratio (%) |  |  |  |  |  |
| Test A | 99.99 or more | 99.99 or more | 99 | 99 | Without effect |
| Test B | 99.99 or more | 99.99 or more | 99 | 99 | Without effect |
| Test C | 99.99 or more | 99.99 or more | 99 | 99 | Without effect |

The filter media 4A of Example 4 was also prepared by using the water and oil repellent, in comparison with the filter media 1A of Example 1. Since the amount of the water and oil repellent was 0.03% by weight, the sterilization ratio and the wet tensile strength did not decrease, and excellent repellency was achieved. In the case of Comparative Example 4 in which the large amount, or 3.0% by weight of the water and oil repellent was used, the sterilization ratio was decreased in the level of 1/100 times in comparison with the filter media of Example 4. The filter media 5Y of Comparative Example 5 in which, in Comparative Example 4, the cationic synthetic resin binder was replaced by nonionic synthetic resin binder, and did not exhibit any sterilizing properties at all. Also its wet tensile strength was decreased remarkably to 0.10 kN/m.

It seems that the water repellent exhibits excellent repellency by extinction of the hydrophilic group (hydroxyl group) on the fiber.

Result 3:

|  | 5A | 6X | 7Y | 8X |
|---|---|---|---|---|
| Fiber material | Rayon fiber having OH group | Rayon fiber having OH group | Rayon fiber having OH group | Rayon fiber having OH group |
| Impregnated Condition | Wet paper web ASHRAE filter media | Wet paper web ASHRAE filter media | Wet paper web ASHRAE filter media | Wet paper web ASHRAE filter media |
| Binder | Cationic | Cationic | None used | Nonionic |
| Enzyme | Modified enzyme | None used | Modified enzyme | Modified enzyme |
| Pressure drop (Pa) | 2.3 | 2.9 | 2.6 | 2.2 |
| 0.3 μm DOP collecting efficiency (%) | 12.50 | 15.00 | 10.90 | 11.80 |
| PF-Value | 24.7 | 23.8 | 24.5 | 24.3 |
| Water repellency (mm: height of water column) | 300 | 50 | 160 | 60 |
| Dry tensile strength (kN/m) | 1.90 | 0.88 | 0.01 or less | 0.39 |

-continued

| Result 3: | | | | |
|---|---|---|---|---|
| | 5A | 6X | 7Y | 8X |
| Wet tensile strength (kN/m) | 0.22 | 0.06 | 0.01 or less | 0.04 |
| Sterilization ratio (%) | | | | |
| Test A | 99.99 or more | Without effect | 99.99 or more | 99 |
| Test B | 99.99 or more | Without effect | 99.99 or more | 99 |
| Test C | 99.99 or more | Without effect | 99.99 or more | 99 |

In case of the Rayon fiber having hydroxyl group as the functional group having the anionic polarity, the combination of the modified enzyme having the cationic polarity and the cationic synthetic resin binder achieves effectively all of the water repellency, the dry tensile strength and the wet tensile strength while maintaining the excellent sterilizing properties in the same manner as the glass fiber. The filter media of Comparative Examples 6 to 8 differed from that of Example 5, namely the filter media do not contain the modified enzyme (Comparative Example 6X), do not contain the binder (Comparative Example 7X) and that do not contain the nonionic binder (Comparative Example 8X), so that they could not achieve the desired properties. In detail, the filter media 6X had neither the water repellency nor the sterilizing property, the filter media 7X had neither the dry tensile strength nor the wet tensile strength, and the filter media 8X had a sterilizing property which is lower than the level of 1/100 of Example 5A, in the level of 100 times. Also its repellency and the dry tensile strength is much lower.

| Result 4: | | | |
|---|---|---|---|
| | 6A | 9X | 10X |
| Fiber material | Glass fiber having OH group | Glass fiber having OH group | Glass fiber having OH group |
| Impregnated Condition | Wet paper web HEPA filter media | Wet paper web HEPA filter media | Wet paper web HEPA filter media |
| Binder | Cationic | Nonionic | Anionic |
| Enzyme | Modified enzyme | Modified enzyme | Modified enzyme |
| Pressure drop (Pa) | 290 | 283 | 288 |
| 0.3 μm DOP collecting efficiency (%) | 99.9945 | 99.9909 | 99.9937 |
| PF-Value | 14.4 | 14.0 | 14.3 |
| Water repellency (mm: height of water column) | 570 | 100 | 60 |
| Dry tensile strength (kN/m) | 1.27 | 0.29 | 0.22 |
| Wet tensile strength (kN/m) | 0.42 | 0.10 | 0.10 |
| Sterilization ratio (%) | | | |
| Test A | 99.99 or more | 99 | 99 |
| Test B | 99.99 or more | 99 | 99 |
| Test C | 99.99 or more | 99 | 99 |

The filter media 6A of Example 6 is an example in which the modified enzyme having the cationic enzyme and the cationic synthetic resin binder were used for the filter media fiber having the anionic polarity, wherein the excellent sterilizing properties, wet tensile strength and water repellency were achieved. In case of the filter media 9X of Comparative Example 9 in which the nonionic synthetic resin binder was used and of the filter media 10X of Comparative Example 10 in which the filter media fiber having the anionic polarity, and the same anionic synthetic resin binder were used, the sterilizing property, the wet tensile strength and the water repellency were very bad.

| Result 5: | | | |
|---|---|---|---|
| | 7A | 11X | 12X |
| Fiber material | Glass fiber having OH group | Glass fiber having OH group | Glass fiber having OH group |
| Impregnated Condition | Wet paper web HEPA filter media | Wet paper web HEPA filter media | Wet paper web HEPA filter media |
| Binder | Cationic | Cationic | Cationic |
| Enzyme | Modified enzyme | Modified enzyme | Modified enzyme |
| Drying Temperature of rotary dryer | 120 | 50 | 230 |
| Pressure drop (Pa) | 288 | 275 | 282 |
| 0.3 μm DOP collecting efficiency (%) | 99.9927 | 99.9987 | 99.9905 |
| PF-Value | 14.1 | 13.9 | 14.0 |
| Water repellency (mm: height of water column) | 530 | 120 | 700 |
| Dry tensile strength (kN/m) | 1.33 | 1.03 | 1.90 |
| Wet tensile strength (kN/m) | 0.42 | 0.11 | 0.69 |
| Sterilization ratio (%) | | | |
| Test A | 99.99 or more | 99.99 or more | 99 |
| Test B | 99.99 or more | 99.99 or more | 99 |
| Test C | 99.99 or more | 99.99 or more | 99 |

Since, in case of Comparative Example 11 in which the temperature of the dry step was 50° C., the immobilization of the modified enzyme through covalent bonding, etc, and development of the strength by the cationic synthetic resin binder was not progressed completely, the wet tensile strength which means water resistance, and the water repellency were developed insufficiently (Filter media 11X). In Comparative Example 12 in which the temperature of the drying step was 230° C., the sterilizing properties of the modified enzyme decreased (Filter media 12X). Therefore, it has known that the temperature of the drying step is preferably from 80 to 220° C.

Result 6:

| | 8A | 13X |
|---|---|---|
| Fiber material | Ion exchange resin fiber having amino group | Ion exchange resin fiber having amino group |
| Impregnated Condtion | Wet paper web ASHRAE filter media | Wet paper web ASHRAE filter media |
| Binder | Anionic | Nonionic |
| Enzyme | Modified enzyme | Modified enzyme |
| Pressure drop (Pa) | 1.0 | 0.9 |
| 0.3 μm DOP collecting efficiency (%) | 5.70 | 5.20 |
| PF-Value | 25.0 | 25.2 |
| Water repellency (mm: height of water column) | 520 | 50 |
| Dry tensile strength (kN/m) | 1.33 | 0.29 |
| Wet tensile strength (kN/m) | 0.37 | 0.04 |
| Sterilization ratio (%) | | |
| Test A | 99.99 or more | 99 |
| Test B | 99.99 or more | 99 |
| Test C | 99.99 or more | 99 |

When the filter media 8A of Example 8 compares with the filter media 13X of Comparative Example 13, it has known that, in the case where the functional group of the filter media fiber is the amino group having the cationic polarity, using the anionic modified enzyme and the anionic synthetic resin binder lead to the excellent sterilizing properties and the wet tensile strength.

Result 7:

| | 1A | 9A | 10A | 11A | 1X |
|---|---|---|---|---|---|
| Fiber material | Glass fiber having OH group | Glass fiber having OH group | Glass fiber having OH group | 70% Glass fiber having OH group, and 30% Ion exchange resin fiber having amino group | Glass fiber having OH group |
| Impregnated Condition | Wet paper web HEPA filter media | Wet paper web HEPA filter media | Wet paper web HEPA filter media | Wet paper web HEPA filter media | Wet paper web HEPA filter media |
| Binder | Cationic | Cationic | Cationic | Cationic | Cationic |
| Enzyme | Modified enzyme | Modified enzyme | Modified enzyme | Modified enzyme | None used |
| Pressure drop (Pa) | 285 | 290 | 280 | 220 | 285 |
| 0.3 μm DOP collecting efficiency (%) | 99.9914 | 99.9937 | 99.9917 | 99.9915 | 99.9914 |
| PF-Value | 14.0 | 14.2 | 14.3 | 14.3 | 14.0 |
| Water repellency (mm: height of water column) | 550 | 540 | 1250 | 620 | 50 |
| Dry tensile strength (kN/m) | 1.27 | 1.18 | 1.45 | 1.20 | 0.64 |
| Wet tensile strength (kN/m) | 0.42 | 0.38 | 0.55 | 0.40 | 0.10 |
| Sterilization ratio (%) | | | | | |
| Test A | 99.99 or more | 99.99 | 99.99 | 99.99 or more | Without effect |
| Test B | 99.99 or more | 99.99 | 99.99 | 99.99 or more | Without effect |
| Test C | 99.99 or more | 99.99 | 99.99 | 99.99 or more | Without effect |

The filter media 9A of Example 9 demonstrates that, when the applied amount of the modified enzyme was decreased, the sterilizing properties decrease, but a sterilization ratio of 99.99% or more is achieved.

The filter media 10A of Example 10 demonstrates that, when the applied amount of the cationic synthetic resin binder was increased, the sterilizing properties decrease, but a sterilization ratio of 99.9% or more is achieved.

The filter media 11A of Example 11 demonstrates that, even if the glass fiber having the hydroxyl group as the functional group having the anionic polarity was used in a mixture with the ion exchange resin fiber having an amino group as the functional group having the cationic polarity, in that case the ionic polarity of the whole glass fiber is the anionic polarity opposite to the ionic polarity of the cationic modified enzyme, and the cationic synthetic resin binder, the sufficient repellency, the sufficient wet tensile strength, and the sufficient sterilizing properties are achieved.

What is claimed is:

1. An air purifying filter media having a dry tensile strength, a wet tensile strength in association with water resistance and water repellency and exhibiting bactericidal/sterilizing or antimicrobial means properties using enzyme reaction, obtained by applying a mixture of the modified enzyme which has an ionic polarity opposite to the ionic polarity of the whole filter media fiber having a functional group and which has sterilizing properties, and an ionic synthetic resin binder having the opposite ionic polarity similar to the modified enzyme, to the whole filter media fiber as described above.

2. The air purifying filter media according to claim 1, wherein the filter media fiber having the functional group is at least one of a group consisting of inorganic fiber, nature fiber or derivative thereof, organic synthetic fiber having at least one of a group consisting of hydroxyl and carboxyl group having an anionic polarity, and an amino or an imino group having a cationic polarity.

3. The air purifying filter media according to claim 1, wherein the filter media fiber is at least one fiber having at least one of a group consisting of a hydroxyl and carboxyl group having an anionic polarity, and an amino or an imino group having a cationic polarity, and selecting from a group consisting the inorganic fiber from boron-silica glass fibers, alkyl amine glass fibers, silica-alumina fibers; the nature fiber or derivative thereof selected from non-wood fiber or wood fibers, namely, rayon fibers, cotton fibers, hemp fibers, wool fibers; the organic synthetic fibers selected from polyamide fibers, polyvinyl alcohol fibers, acetate fibers, polyacrylamide fibers or copolymer thereof.

4. The air purifying filter media according to claim 1, wherein the modified enzyme being immobilized on the functional group of the filter media fiber is at least one modified enzyme modified with at least one compound selected from a group consisting of N-substituted carbamate bromide, N-substituted imide carbonate bromide, acetyl bromide + triacetyl cellulose, dimethylaminoethyl, diethylaminoethyl, protamine, polyethylene imine, polyvinyl amine, polyallyl amine, polylysine, polyomitine, dextran, dextran sulfate, dextrin and chondroitin sulfate.

5. The air purifying filter media according to claim 1, wherein the to be modified enzyme, is at least one selected from a group consisting of β-1,3-glucanase, chitinase, lysozyme, protease, glucosidase, β-galactosidase, endo-β-N-acetylglucosamidase and endolysin.

6. The air purifying filter media according to claim 1, wherein the ionic synthetic resin binder is at least one selected from a group consisting of acrylic resin, urethane resin, vinyl acetate resin, SBR resin, Epoxy resin, polyvinyl alcohol resin.

7. The air purifying filter media according to claim 1, wherein the used amount of the modified enzymes is 0.01% by weight or more, based on the weight of the filter media.

8. The air purifying filter media according to claim 1, wherein the used amount of the ionic synthetic resin binder is 0.1 to 10.0% by weight, based on the weight of the filter media.

9. The air purifying filter media according to claim 1, wherein the dry tensile strength of the filter media, measured according to MIL-F-51079 C, is 0.45 kN/m or more in a machine direction of the filter media and 0.35 kN/m or more in a cross direction of the filter media.

10. The air purifying filter media according to claim 1. wherein the wet tensile strength of the filter media, measured according to MIL-F-51079 C, is 0.176 kN/m or more in a cross direction of the filter media.

11. The air purifying filter media according to claim 1, wherein the water repellency of the filter media comprising the glass fiber as main component, measured according to MIL282, is 150mm or more (the height of the water column).

12. The air purifying filter media according to claim 1, wherein the main component of the filter media fiber is selected from the nature fiber or derivative thereof selected from non-wood fiber or wood fibers, namely, rayon fibers, cotton fibers, hemp fibers, wool fibers; the organic synthetic fibers selected from polyamide fibers, polyvinyl alcohol fibers, acetate fibers, polyacrylamide fibers or copolymer thereof, and the water repellency of the filter media, measured according to MIL-282, is 100mm or more (the height of the water column).

13. The air purifying filter media according to claim 1, wherein the sterilization ratio is 99.9% or more.

14. The air purifying filter media according to claim 1, wherein other than the modified enzyme and the ionic synthetic resin binder, the water repellent agent is additionally applied.

15. The air purifying filter media according to claim 14, wherein the applied amount of the water repellent agent is 0.1% by weight or less, based on the filter media.

16. The air purifying filter media according to claim 1, wherein in addition to the ionic synthetic resin binder an internal fibrous binder is used.

17. The air purifying filter media according to claim 2, wherein the filter media fiber is at least one fiber having at least one of a group consisting of a hydroxyl and carboxyl group having an anionic polarity, and an amino or an imino group having a cationic polarity, and selecting from a group consisting the inorganic fiber from boron-silica glass fibers, alkyl amine glass fibers, silica-alumina fibers; the nature fiber or derivative thereof selected from non-wood fiber or wood fibers, namely, rayon fibers, cotton fibers, hemp fibers, wool fibers; the organic synthetic fibers selected from polyamide fibers, polyvinyl alcohol fibers, acetate fibers, polyacrylamide fibers or copolymer thereof.

18. The air purifying filter media according to claim 2, wherein the modified enzyme being immobilized on the functional group of the filter media fiber is at least one modified enzyme modified with at least one compound selected from a group consisting of N-substituted carbamate bromide, N-substituted imide carbonate bromide, acetyl bromide + triacetyl cellulose, dimethylaminoethyl, diethylaminoethyl, protamine, polyethylene imine, polyvinyl amine, polyallyl amine, polylysine, polyornitine, dextran, dextran sulfate, dextrin and chondroitin sulfate.

19. The air purifying filter media according to claim 2, wherein the to be modified enzyme is at least one selected from a group consisting of β1,3-glucanase, chitinase, lysozyme, protease, glucosidase, β-galactosidase, endo-β-N-acetylglucosamidase and endolysin.

20. The air purifying filter media according to claim 4, wherein the to be modified enzyme is at least one selected from a group consisting of β-1,3-glucanase, chitinase, lysozyme, protease, glucosidase, β-galactosidase, endoβ-N-acetylglucosamidase and endolysin.

21. The air purifying filter media according to claim 2, wherein the ionic synthetic resin binder is at least one selected from a group consisting of acrylic resin, urethane resin, vinyl acetate resin, SBR resin, Epoxy resin, polyvinyl alcohol resin.

22. The air purifying filter media according to claim 3, wherein the ionic synthetic resin binder is at least one selected from a group consisting of acrylic resin, urethane resin, vinyl acetate resin, SBR resin, Epoxy resin, polyvinyl alcohol resin.

23. The air purifying filter media according to claim 4, wherein the ionic synthetic resin binder is at least one selected from a group consisting of acrylic resin, urethane resin, vinyl acetate resin, SBR resin, Epoxy resin, polyvinyl alcohol resin.

24. The air purifying filter media according to claim 5, wherein the ionic synthetic resin binder is at least one selected from a group consisting of acrylic resin, urethane resin, vinyl acetate resin, SBR resin, Epoxy resin, polyvinyl alcohol resin.

25. The air purifying filter media according to claim 2, wherein the used amount of the modified enzymes is 0.01% by weight or more, based on the weight of the filter media.

26. The air purifying filter media according to claim 4, wherein the used amount of the modified enzymes is 0.01% by weight or more, based on the weight of the filter media.

27. The air purifying filter media according to claim 5, wherein the used amount of the modified enzymes is 0.01% by weight or more, based on the weight of the filter media.

28. The air purifying filter media according to claim 2, wherein the used amount of the ionic synthetic resin binder is 0.1 to 10.0% by weight, based on the weight of the filter media.

29. The air purifying filter media according to claim 6, wherein the used amount of the ionic synthetic resin binder is 0.1 to 10.0% by weight, based on the weight of the filter media.

30. The air purifying filter media according to claim 7, wherein the used amount of the ionic synthetic resin binder is 0.1 to 10.0% by weight, based on the weight of the filter media.

31. The air purifying filter media according to claim 2, wherein the dry tensile strength of the filter media, measured according to MIL-F-51079 C, is 0.45 kN/m or more in a machine direction of the filter media and 0.35 kN/m or more in a cross direction of the filter media.

32. The air purifying filter media according to claim 8, wherein the dry tensile strength of the filter media, measured according to MIL-F-51079 C, is 0.45 kN/m, or more in a machine direction of the filter media and 0.35 kN/m or more in a cross direction of the filter media.

33. The air purifying filter media according to claim 30, wherein the dry tensile strength of the filter media, measured according to MIL-F-51079 C, is 0.45 kN/m or more in a machine direction of the filter media and 0.35 kN/m or more in a cross direction of the filter media.

34. The air purifying filter media according to claim 2, wherein the wet tensile strength of the filter media, measured according to MIL-F-51079 C, is 0.176 kN/m or more in a cross direction of the filter media.

35. The air purifying filter media according to claim 6, wherein the wet tensile strength of the filter media, measured according to MIL-F-51079 C, is 0.176 kN/m or more in a cross direction of the filter media.

36. The air purifying filter media according to claim 8, wherein the wet tensile strength of the filter media, measured according to MIL-F-51079 C, is 0.176 kN/m or more in a cross direction of the filter media.

37. The air purifying filter media according to claim 30, wherein the wet tensile strength of the filter media, measured according to MIL-F-51079 C, is 0.176 kN/m or more in a cross direction of the filter media.

38. The air purifying filter media according to claim 2, wherein the water repellency of the filter media comprising the glass fiber as main component, measured according to MIL-282, is 150mm or more (the height of the water column).

39. The air purifying filter media according to claim 4, wherein the water repellency of the filter media comprising the glass fiber as main component, measured according to MIL-282, is 150mm or more (the height of the water column).

40. The air purifying filter media according to claim 5, wherein the water repellency of the filter media comprising the glass fiber as main component, measured according to MIL-282, is 150mm or more (the height of the water column).

41. The air purifying filter media according to claim 8, wherein the water repellency of the filter media comprising the glass fiber as main component, measured according to MIL-282, is 150mm or more (the height of the water column).

42. The air purifying filter media according to claim 30, wherein the water repellency of the filter media comprising the glass fiber as main component, measured according to MIL-282, is 150mm or more (the height of the water column).

43. The air purifying filter media according to claim 2, wherein the main component of the filter media fiber is selected from the nature fiber or derivative thereof selected from non-wood fiber or wood fibers, namely, rayon fibers, cotton fibers, hemp fibers, wool fibers; the organic synthetic fibers selected from polyamide fibers, polyvinyl alcohol fibers, acetate fibers, polyacrylamide fibers or copolymer thereof, and the water repellency of the filter media, measured according to MIL-282, is 100mm or more (the height of the water column).

44. The air purifying filter media according to claim 4, wherein the main component of the filter media fiber is selected from the nature fiber or derivative thereof selected from non-wood fiber or wood fibers, namely, rayon fibers, cotton fibers, hemp fibers, wool fibers; the organic synthetic fibers selected from polyamide fibers, polyvinyl alcohol fibers, acetate fibers, polyacrylamide fibers or copolymer thereof, and the water repellency of the filter media, measured according to MIL-282, is 100mm or more (the height of the water column).

45. The air purifying filter media according to claim 5, wherein the main component of the filter media fiber is selected from the nature fiber or derivative thereof selected from non-wood fiber or wood fibers, namely, rayon fibers, cotton fibers, hemp fibers, wool fibers; the organic synthetic fibers selected from polyamide fibers, polyvinyl alcohol fibers, acetate fibers, polyacrylamide fibers or copolymer thereof, and the water repellency of the filter media, measured according to MIL-282, is 100mm or more (the height of the water column).

46. The air purifying filter media according to claim 8, wherein the main component of the filter media fiber is selected from the nature fiber or derivative thereof selected from non-wood fiber or wood fibers, namely, rayon fibers, cotton fibers, hemp fibers, wool fibers; the organic synthetic fibers selected from polyamide fibers polyvinyl alcohol fibers, acetate fibers, polyacrylamide fibers or copolymer thereof, and the water repellency of the filter media, measured according to MIL-282, is 100mm or more (the height of the water column).

47. The air purifying filter media according to claim 30, wherein the main component of the filter media fiber is selected from the nature fiber or derivative thereof selected from non-wood fiber or wood fibers, namely, rayon fibers, cotton fibers, hemp fibers, wool fibers; the organic synthetic fibers selected from polyamide fibers, polyvinyl alcohol fibers, acetate fibers, polyacrylamide fibers or copolymer thereof, and the water repellency of the filter media, measured according to MIL-282, is 100mm or more (the height of the water column).

48. The air purifying filter media according to claim 2, wherein the sterilization ratio is 99.9% or more.

49. The air purifying filter media according to claim 4, wherein the sterilization ratio is 99.9% or more.

50. The air purifying filter media according to claim 5, wherein the sterilization ratio is 99.9% or more.

51. The air purifying filter media according to claim 6, wherein the sterilization ratio is 99.9% or more.

52. The air purifying filter media according to claim 7, wherein the sterilization ratio is 99.9% or more.

53. The air purifying filter media according to claim 8, wherein the sterilization ratio is 99.9% or more.

54. The air purifying filter media according to claim 30, wherein the sterilization ratio is 99.9% or more.

55. The air purifying filter media according to claim 2, wherein other than the modified enzyme and the ionic synthetic resin binder, the water repellent agent is additionally applied.

56. The air purifying filter media according to claim 2, wherein the applied amount of the water repellent agent is 0.1% by weight or less, based on the filter media.

57. The air purifying filter media according to one from claim 2, wherein in addition to the ionic synthetic resin binder an internal fibrous binder is used.

58. The air purifying filter media according to one from claim 9, wherein in addition to the ionic synthetic resin binder an internal fibrous binder is used.

59. The air purifying filter media according to one from claim 10, wherein in addition to the ionic synthetic resin binder an internal fibrous binder is used.

* * * * *